(12) United States Patent
Katsevich et al.

(10) Patent No.: US 10,617,365 B2
(45) Date of Patent: *Apr. 14, 2020

(54) SYSTEM AND METHOD FOR MOTION ESTIMATION USING ARTIFICIAL INTELLIGENCE IN HELICAL COMPUTED TOMOGRAPHY

(71) Applicants: University of Central Florida Research Foundation, Inc., Orlando, FL (US); iTomography Corporation, Barker, TX (US); Canon Medical Systems Corporation, Otawara-shi (JP)

(72) Inventors: Alexander Katsevich, Oviedo, FL (US); Michael Frenkel, Barker, TX (US); Victor Prieto, Houston, TX (US); Zhou Yu, Wilmette, IL (US)

(73) Assignees: University of Central Florida Research Foundation, Inc., Orlando, FL (US); iTomography Corporation, Barker, TX (US); Canon Medical Systems Corporation, Otawara-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/412,290

(22) Filed: May 14, 2019

(65) Prior Publication Data

US 2019/0328341 A1  Oct. 31, 2019

Related U.S. Application Data

(63) Continuation-in-part of application No. 15/815,662, filed on Nov. 16, 2017, now Pat. No. 10,339,678.

(Continued)

(51) Int. Cl.
G06K 9/00 (2006.01)
A61B 6/03 (2006.01)
(Continued)

(52) U.S. Cl.
CPC .............. *A61B 6/032* (2013.01); *A61B 6/486* (2013.01); *A61B 6/5211* (2013.01); *G06N 3/08* (2013.01);
(Continued)

(58) Field of Classification Search
None
See application file for complete search history.

(56) References Cited

U.S. PATENT DOCUMENTS

| 2010/0202583 A1 | 8/2010 | Wang et al. |
| 2011/0142313 A1 | 6/2011 | Pack et al. |
| 2016/0256127 A1 | 9/2016 | Lee et al. |

OTHER PUBLICATIONS

Kim et al., Cardiac motion correction based on partial angle reconstructed images in x-ray CT. Med. Phys. 2015. vol. 42 (No. 5): 2560-2571.

(Continued)

*Primary Examiner* — Atiba O Fitzpatrick
(74) *Attorney, Agent, or Firm* — Molly L. Sauter; Smith & Hopen, P.A.

(57) ABSTRACT

An improved system and method for estimating and compensating for motion by reducing motion artifacts produced during image reconstruction from helical computed tomography (CT) scan data. In a particular embodiment, the reconstruction may be based on helical partial angle reconstruction (PAR) and the registration may be performed utilizing one or more artificial intelligence (AI) based methods.

20 Claims, 8 Drawing Sheets

Related U.S. Application Data

(60) Provisional application No. 62/423,166, filed on Nov. 16, 2016.

(51) Int. Cl.
  *G06N 3/08* (2006.01)
  *A61B 6/00* (2006.01)
  *G06T 7/00* (2017.01)
  G06T 7/38 (2017.01)
  G06T 11/00 (2006.01)

(52) U.S. Cl.
  CPC .......... *G06T 7/0012* (2013.01); *A61B 6/4085* (2013.01); *A61B 6/5264* (2013.01); *A61B 6/563* (2013.01); *G06T 7/38* (2017.01); *G06T 11/005* (2013.01); *G06T 2207/10081* (2013.01); *G06T 2211/412* (2013.01)

(56) References Cited

OTHER PUBLICATIONS

International Search Report & Written Opinion for PCT/US17/62115, filing date: Nov. 16, 2017, dated Feb. 13, 2018; Applicant: University of Central Florida Research Foundation, Inc. et al.

International Preliminary Report on Patentability for PCT/US17/62115m, filing date: Nov. 16, 2017, dated Nov. 16, 2016; Applicant: University of Central Florida Research Foundation, Inc. et al.

SYSTEM AND METHOD FOR MOTION ESTIMATION USING ARTIFICIAL INTELLIGENCE IN HELICAL COMPUTED TOMOGRAPHY

CROSS-REFERENCE TO RELATED APPLICATIONS

This application claims priority to U.S. patent application Ser. No. 15/815,662 entitled, "System and Method for Motion Estimation and Compensation in Helical Computed Tomography", filed on Nov. 16, 2017 and to U.S. Provisional Patent Application No. 62/423,166 entitled, "System and Method for Motion Estimation and Compensation in Helical Computed Tomography", filed on Nov. 16, 2016, both of which are incorporated by reference in their entirety.

BACKGROUND OF THE INVENTION

The present invention relates to the field of image processing, and in particular to image processing in medical applications. In particular, the present invention is directed to a deep-leaning based method for motion estimation and motion compensation of a helical computed tomography (CT) scan of an object of interest.

Motion is one of the most critical sources of artifacts in helical cone-beam computed tomography (CT). Motion artifacts result from discrepancies between the requirement that the object remain unchanged during the scan and reality, in which the object changes ("deforms" or "moves") during the scan. Motion of the patient, whether voluntary or involuntary, during image acquisition may result in motion artifacts in the reconstructed image. Involuntary motion, such as respiration or cardiac motion, may result in motion artifacts. While there are techniques known in the art for the reconstruction of motion compensated images from circular CT scan data, the known techniques do not address the unique conditions of a helical CT scan, wherein the field of view (FOV) is continuously changing.

Accordingly, what is needed in the art is an improved system and method for motion estimation and compensating for motion by reducing motion artifacts produced during image reconstruction from helical computed tomography (CT) scan data.

SUMMARY OF THE INVENTION

The present invention provides an improved system and method for estimating motion and compensating for motion by reducing motion artifacts produced during image reconstruction from helical computed tomography scan data. In various embodiments, the system and method can also be applied to more general helical-like trajectories, including variable pitch helices and helices in which the axis of rotation changes.

In one embodiment, the present invention provides a method for estimating and compensating for motion by reducing motion artifacts in an image reconstruction from helical computed tomography (CT) scan data of an object of interest, which includes, collecting helical computer tomography (CT) scan data of an object of interest, wherein the scan data is acquired using a radiation source to generate a cone beam and a radiation detector to detect the cone beam. The method further includes, selecting a plurality of center-points along a trajectory of the radiation source and identifying a plurality of pairs of sections along the trajectory of the radiation source, wherein each of the plurality of pairs of sections is associated with one of the plurality of center-points and wherein a first section of each of the pairs of sections and a second section of each of the pairs of sections are positioned on opposite sides of the center-point. In a particular embodiment, the sections are separated from each other by an angular distance equal to $\pi$. The method additionally includes, selecting a subset of the plurality of pairs of sections and reconstructing, for each pair of the subset, a first partial image from the scan data of the first section and a second partial image from the scan data of the second section and performing image registration of the first partial image and the second partial image for each pair of the subset to estimate a deformation that transforms the first partial image into the second partial image, wherein the deformation is representative of motion of the object of interest during the scan. Following image registration of the partial images, the method further includes, generating a motion compensated image by reconstructing the object of interest using the scan data and the estimated deformation.

In an additional embodiment, the invention provides a system for estimating and compensating for motion by reducing motion artifacts in an image reconstruction from helical computed tomography (CT) scan data of an object of interest. The system includes, a memory for storing a helical computer tomography (CT) scan data of an object of interest and a data processor. The data processor is configured for estimating and compensating for motion by reducing motion artifacts in an image reconstruction from the helical computed tomography (CT) scan data of an object of interest. As such, the data processor is adapted for loading the helical CT scan data from the memory, selecting a plurality of center-points along a trajectory of the radiation source and identifying a plurality of pairs of sections along the trajectory of the radiation source, wherein each of the plurality of pairs of sections is associated with one of the plurality of center-points and wherein a first section of each of the pairs of sections and a second section of each of the pairs of sections are positioned on opposite sides of the center-point. In a particular embodiment, the sections are separated from each other by an angular distance equal to $\pi$. The data processor is further configured for selecting a subset of the plurality of pairs of sections and for reconstructing, for each pair of the subset, a first partial image from the scan data of the first section and a second partial image from the scan data of the second section, for performing image registration of the first partial image and the second partial image for each pair of the subset to estimate a deformation that transforms the first partial image into the second partial image, wherein the deformation is representative of motion of the object of interest during the scan, for generating a motion artifact compensated image by reconstructing the object of interest using scan data and the estimated deformation.

The present invention additionally provides an embodiment including one or more non-transitory computer-readable media having computer-executable instructions for performing a method of estimating and compensating for motion by reducing motion artifacts in an image reconstruction from helical computed tomography (CT) scan data of an object of interest. The method includes, collecting helical computer tomography (CT) scan data of an object of interest, wherein the scan data is acquired using a radiation source to generate a cone beam and a radiation detector to detect the cone beam. The method further includes, selecting a plurality of center-points along a trajectory of the radiation source and identifying a plurality of pairs of sections along the trajectory of the radiation source, wherein each of the plurality of pairs of sections is associated with one of the plurality of center-points and wherein a first section of each of the pair of sections and a second section of each of the pair of sections are positioned on opposite sides of the center-point. In a particular embodiment, the sections are separated from each other by an angular distance equal to π. The method additionally includes, selecting a subset of the plurality of pairs of sections and reconstructing, for each pair of the subset, a first partial image from the scan data of the first section and a second partial image from the scan data of the second section and performing image registration of the first partial image and the second partial image for each pair of the subset to estimate a deformation that transforms the first partial image into the second partial image, wherein the deformation is representative of motion of the object of interest during the scan. Following image registration of the partial images, the method further includes, generating a motion artifact compensated image by reconstructing the object of interest using scan data and the estimated deformation.

In a particular embodiment, image registration may be performed using an artificial intelligence based method and in specific embodiments, the image registration may be performed using a Deep Learning based method or a Convolutional Neural Network (CNN) based method.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
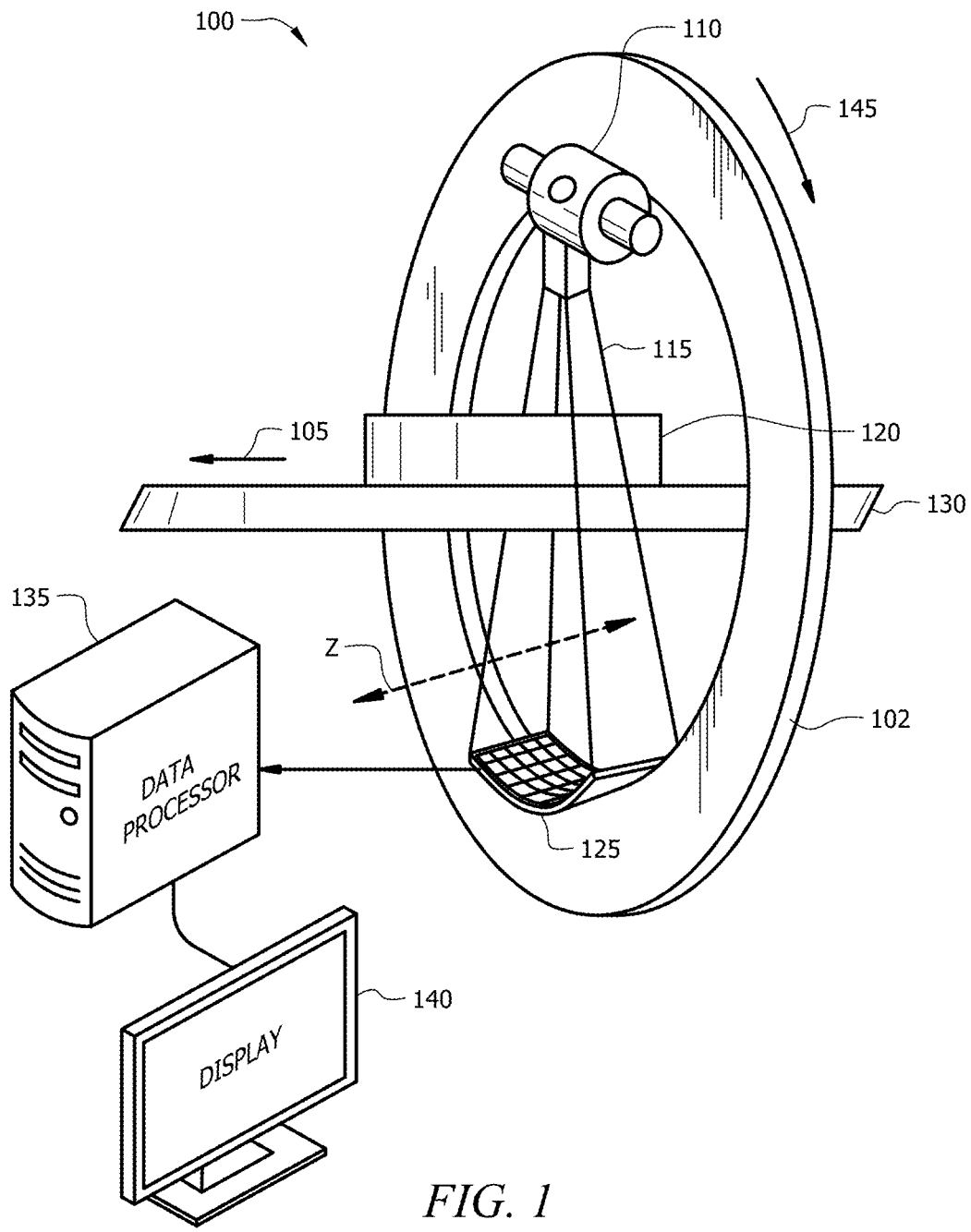
FIG. 1 is an illustration of an exemplary helical computer tomography (CT) scanner, in accordance with an embodiment of the present invention.

FIG. 1 illustrates an exemplary embodiment of a helical CT scanner system 100 according to the present invention. This embodiment is intended to be exemplary and the present invention will be described as relating to medical imaging. However, this is not intended to be limited and various embodiments of the present invention may also be used for other purposes, such as baggage scanning for security and material analysis.

As shown in FIG. 1, a helical CT scanner system 100 includes a gantry 102 which is rotatable around a rotational axis 105. The gantry 102 carries a radiation source 110 that forms a cone shaped radiation beam 115. The radiation beam 115 emitted from the radiation source 110 is focused on an object of interest 120 positioned in the center of the gantry 102. A radiation detector 125 is positioned on the gantry 102 opposite from the radiation source 110. The radiation detector 125 comprises a plurality of detector elements for measuring the intensity of the cone shaped radiation beam 115 after it passes through the object of interest 120.

During a scan of the object of interest 120, the radiation source 110 and the radiation detector 125 are rotated with the gantry 102 in a direction indicated 145. The object of interest 120 is additionally positioned on a movable table 130 which moves the object of interest 120 along a direction parallel to the rotational axis 105 of the gantry 102. As such, helical scan trajectory is created around the object of interest 120 and helical CT scan data of the object of interest is obtained.

Following the helical scanning of the object of interest 120, the radiation detector 125 provides the collected helical CT scan data to a data processor 135. The data processor 135 is adapted for reconstructing an image from the measurements provided by the radiation detector 125. The image generated by the data processor 135 may then be provided to a display 140 for subsequent viewing.

The data processor 135 is additionally adapted to perform motion estimation and motion compensation to correct for motion in the scan data provided by the radiation detector 125. Motion estimation and compensation may be performed by the data processor 135 as detailed below.

In the case of a relatively long helical scan trajectory C, each voxel $\vec{x}=(x_1, x_2, x_3)$ is reconstructed using its own section of C, denoted as $C(\vec{x})$. Suppose that the parametric description of C is $\vec{y}(s)$. Let $I(\vec{x})$ be the parametric interval corresponding to $C(\vec{x})$. In a helical CT scan, usually, the source of radiation moves along the scan trajectory C with a constant speed, so that the parameter s may be identified with time. Let $f(\vec{x}, s)$ denote the dynamic object, wherein s represents time. It is therefore implied that for every voxel $\vec{x}$, the value of $f$ is reconstructed not at some reference time $s_0$, which is the same for all $\vec{x}$, but at some time $s_{eff}(\vec{x})$, wherein $s_{eff}(\vec{x})$ is the midpoint of the interval $I(\vec{x})$. Accordingly, in the case of helical scanning it is desired to reconstruct only the function $f(\vec{x}, s_{eff}(\vec{x}))$.

In a circular scan, the source "sees" the same FOV (field of view) at all times, and this allows one to reconstruct $f(\vec{x}, s_{ref})$. In contrast, in a helical scan, the FOV constantly changes. This explains the difference between a circular scan and a helical scan and why a different motion artifact estimation and compensation method is required.

Figure 2:
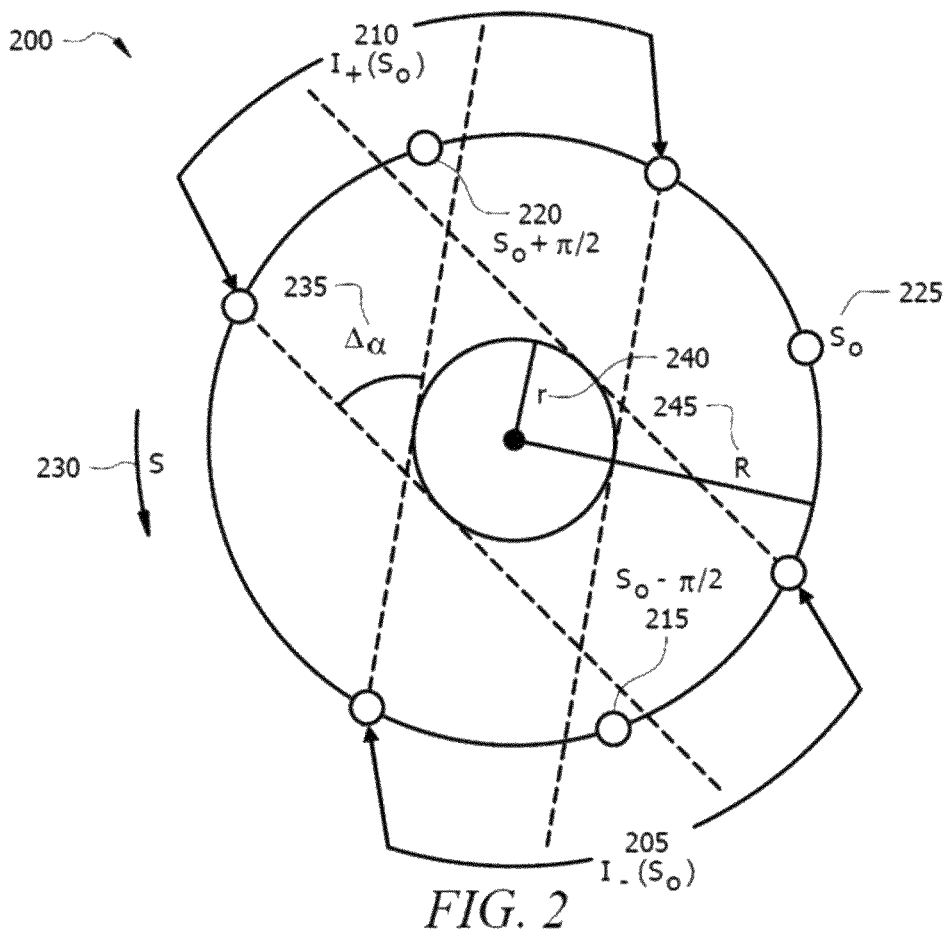
FIG. 2 is an illustration of a portion of a helical trajectory and associated section pairs for estimating motion artifacts in a helical CT scan, in accordance with an embodiment of the present invention. The source trajectory is shown projected onto the plane perpendicular to the rotation axis.

With reference to FIG. 2, it is necessary to find a volume which can be reconstructed using two sections of the helix 200 located at a distance Tr apart. As shown in FIG. 2, referring to these two sections of the helix by their corresponding parametric intervals as $I_-$ and $I_+$, interval $I_-$ 205 is centered at the point $s_0-\pi/2$, 215 and the interval $I_+$ 210 is centered at the point $s_0+\pi/2$ 220. S 230 identifies the direction of rotation of the scan. As a result of symmetry, if motion estimation (ME) is performed based on the partial angle reconstructions (PARs) computed from the two intervals, then the estimated motion model will correspond to the time $s_0$ 225.

Assume that $\Delta_\alpha$ 235 represents the range of directions (in the parallel beam geometry) that is used for computing PARs, as shown in FIG. 2. Let $\Delta_\gamma := \sin^{-1}(r/R)$ be half the fan angle of the ROI (region of interest), wherein r is the center radius 240 and R 245 is the source-to-center of rotation distance. As such, $$I_-(s_0):=[(s_0-\pi/2)-(\Delta_\alpha/2+\Delta_\gamma),(s_0-\pi/2)+(\Delta_\alpha/2+\Delta_\gamma)]$$

$$I_+(s_0):=[(s_0+\pi/2)-(\Delta_\alpha/2+\Delta_\gamma),(s_0+\pi/2)+(\Delta_\alpha/2+\Delta_\gamma)] \quad (1)$$

Thus, the width of each s-interval is $\Delta_\alpha+2\Delta_\gamma$.

Figure 3:
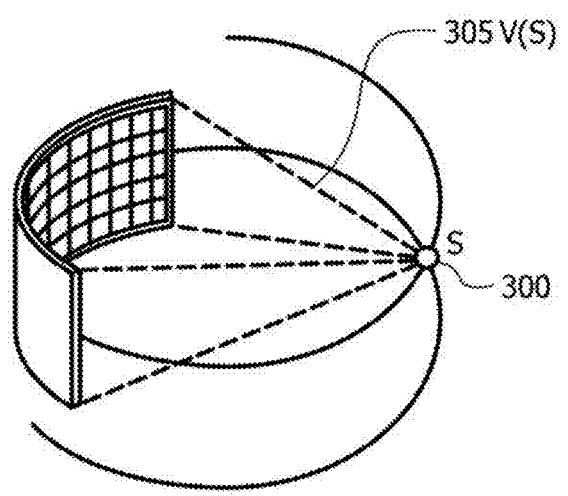
FIG. 3 is an illustration of an auxiliary reconstruction volume for compensating for motion by reducing motion artifacts, in accordance with an embodiment of the present invention. The illustrated volume is visible from one source position.

Once the mid-point $s_0$ is fixed, the desired volume is the set of points x that are "visible" from all source positions $s \in I_\pm(s_0)$. Let V(s) 305 denote the set of points visible when the source is located at s 300, as shown in FIG. 3, then:

$$V_-(s_0)=\cup_{s \in I_-(s_0)} V(s), V_+(s_0)=\cup_{s \in I_+(s_0)} V(s) \quad (2)$$

Figure 4:
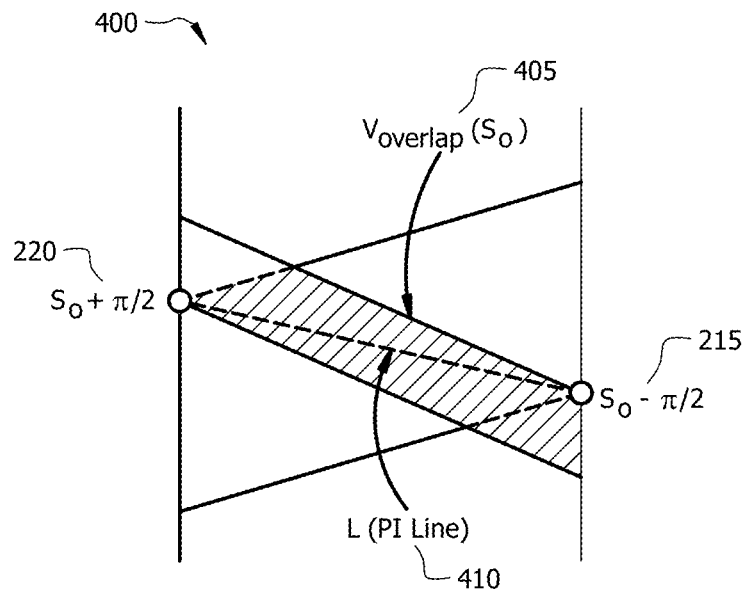
FIG. 4 is an illustration of the overlap of volumes visible from the section pairs for estimating motion artifacts in a helical CT scan, in accordance with an embodiment of the present invention.

Then, the desired volume is $V_{overlap}(s_0)=V_-(s_0) \cap V_+(s_0)$. A vertical cross-section 400 through $V_{overlap}(s_0)$, 405 is illustrated in FIG. 4. Since it is desirable to run the scan with a high pitch value, it is clear that the volume $V_{overlap}(s_0)$ 405 is located rather close to the PI lines 410, and additionally PI lines 500 in FIG. 5., with one endpoint located inside $I_-(s_0)$, and the other endpoint located inside $I_+(s_0)$, as illustrated by one such PI line in FIG. 4.

Figure 5:
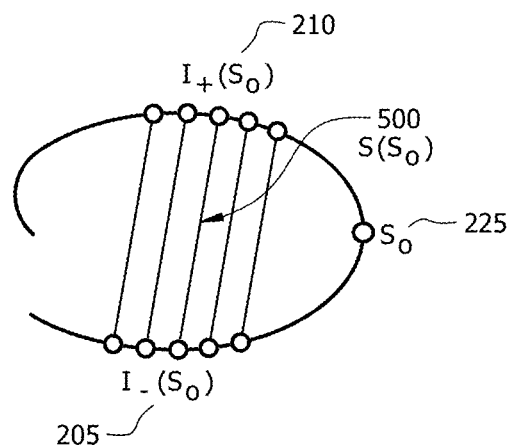
FIG. 5 is an illustration of the PI lines within the overlap volume, in accordance with an embodiment of the present invention.

Letting L (a, b) be the PI line passing through the points $\vec{y}(a)$, $\vec{y}(b)$, the following surface $S(s_0)$ 500 (sometimes referred to as a "potato chip") can be defined, as shown in FIG. 5:

$$S(s_0) := \cup_{|t|<\frac{\Delta_\alpha}{2}+\Delta_\gamma} L(s_0-\pi/2-t, s_0+\pi/2+t). \quad (3)$$

The PI lines in (Eq. 3) have the following properties: their bottom endpoints are in $I_-(s_0)$ 205, their top endpoints are in $I_+(s_0)$ 210, and they are symmetric about $s_0$ 225. When the helical pitch is high, $V_{overlap}(s_0)$ 405 is a fairly "thin" set containing $S(s_0)$ 500. As such, the potato chips, $S(s_0)$ 500 for different $s_0$ 225 do not intersect.

Based on the previous discussion, the present invention provides a method for motion estimation, which includes, first, choose a set of equispaced points, $s_l$, l=1, 2, ..., L, covering the entire scan length and denote the reconstruction grid as $(x_i, y_j, z_k)$.

Second, perform motion estimation, which includes:
1) Loop over all $s_l$. For each $s_l$ repeat the following steps.
2) For each $(x_i, y_j)$, find $z_{ij}=z(x_i, y_j, s_l)$ such that the midpoint of the PI interval of the voxel $(x_i,y_j,z_{ij})$ coincides with $s_l$. Thus, $(x_i,y_j,z_{ij}) \in S(s_l)$, with reference to Eq. 3. Also, find the top and bottom boundaries of $V_{overlap}(s_l)$ above $(x_i,y_j)$.
3) Reconstruct two PARs $f_-$ and $f_+$ using the intervals $I_-(s_l)$ and $I_+(s_l)$, respectively. The PARs will be reconstructed in the coordinates (x, y, h). These coordinates are converted to physical coordinates by the formula $(x, y, h) \rightarrow (x, y, z(x,y,s_l)+h)$. The value of h is constrained to the interval $|h|<H$, where H is sufficiently small so that the resulting volume is strictly inside of $V_{overlap}(s_l)$.

4) Perform image registration by finding the shifts $\vec{\Delta}_{ij}$.

$$\vec{\Delta}_{ij} = \arg\min \Sigma_{ij} [f_+((x_i,y_j,h=0)+\vec{\Delta}_{ij})-f_-((x_i,y_j,h=0)-\vec{\Delta}_{ij})]^2. \quad (4)$$

In discussing the geometric meaning of the minimization problem shown in Eq. 4, recall that the points $(x_i,y_j,h=0)$ all belong to the surface $S(s_l)$. The term $f_+((x_i,y_j,h=0)+\vec{\Delta}_{ij})$ then corresponds to the values of the symmetrically distorted surface $((x_i,y_j,h=0)-\vec{\Delta}_{ij})$ inside the volume $f_-$. By solving Eq. 4, it is guaranteed that the values of $f_+$ and $f_-$ on the two distorted surfaces coincide. Once a solution to Eq. 4 is found, it is assumed that the points on the surface $S(s_l)$ move according the following formula:

$$(x_i, y_j, z_{ij}) \rightarrow (x_i, y_j, z_{ij}) + \vec{\Delta}_{ij} \frac{s-s_l}{\pi/2}. \quad (5)$$

Since the sets $V_{overlap}(s_l)$ are fairly thin, one option is to register two surfaces rather than two volumes.

For additional noise stability, it may be required that motion vectors $\vec{\Delta}_{ij}$ be two-dimensional, i.e., have zero h-component. This way, Eq. 4 is equivalent to registering two 2D images. The downside of this approach is that motion away from the surface $S(s_1)$ is ignored. If motion vectors $\vec{\Delta}_{ij}$ are 3D, then the accuracy of the motion estimation is increased, but noise stability is decreased.

Since the problems of Eq. 4 are independent from each other for all l=1, 2, ..., to insure that the estimated motion vectors change smoothly from one l to the next, the problems of Eq. 4 can be combined for all l and a regularizer can be added that enforces smoothness of $\vec{\Delta}_{ij}(s_l)$ along l.

The third step involves motion-compensated reconstruction. It is proposed that the most straight forward motion compensation reconstruction can be used, wherein motion is accounted for at the backprojection step. Thus, when reconstructing, all that is necessary is to find where any given voxel is located at the current time. This can be done by using the following method steps:
1) Given a voxel $(x_i, y_j, z_k)$, find its PI line.
2) Compute the mid-point $s_{mid}$ of the PI parametric interval of the voxel. This implies that $(x_i, y_j, z_k) \in S(s_{mid})$. In other words, the potato chip containing the given voxel is found.
3) Find the interval $[s_l, s_{l+1}]$ containing $(s_{mid})$.
4) Find the motion vector $\vec{\Delta}_{ij}(s_{mid})$ of the voxel by interpolating between $\vec{\Delta}_{ij}(s_l)$ and $\vec{\Delta}_{ij}(s_{l+1})$.
5) For a given source position/time s, the new position of the voxel is calculated by using the following formula, with reference to Eq. 5:

$$(x_i, y_j, z_k) \rightarrow (x_i, y_j, z_k) + \vec{\Delta}_{ij}(s_{mid}) \frac{s-s_{mid}}{\pi/2}. \quad (6)$$

Figure 6:
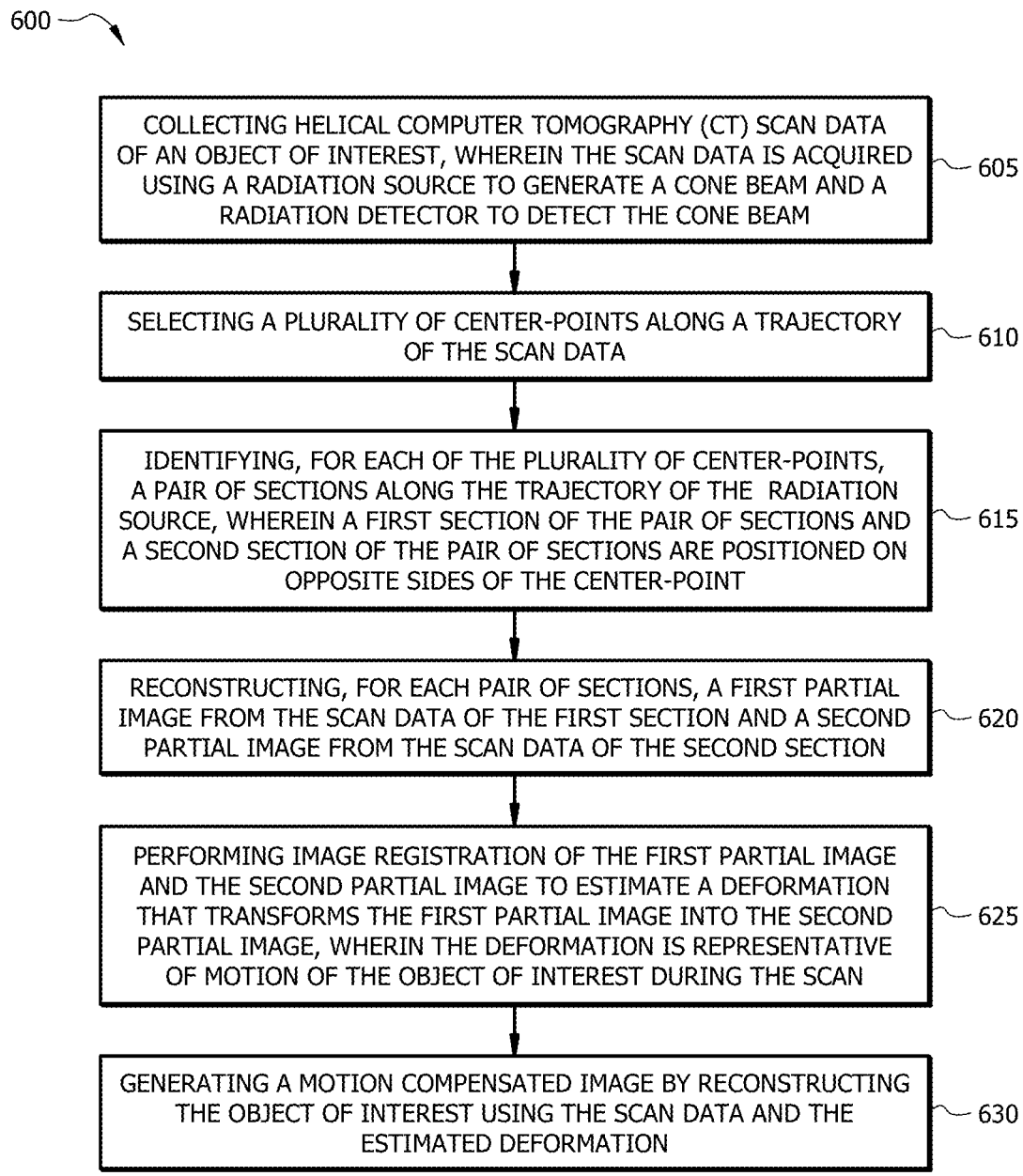
FIG. 6 is a flow diagram illustrating a method for motion estimation and compensation in a helical CT scan, in accordance with an embodiment of the present invention.

With reference to FIG. 6, a method for estimating and compensating for motion by reducing motion artifacts in an image reconstruction from helical computed tomography (CT) scan data of an object of interest is provided 600. The method 600 may be implemented using the data processor 135, the radiation source 110 and the radiation detector 125 of FIG. 1.

At a first step 605, the method 600 includes collecting helical computer tomography (CT) scan data of an object of interest, wherein the scan data is acquired using a radiation source to generate a cone beam and a radiation detector to detect the cone beam.

Following the collection of scan data, the method continues at step 610 by selecting a plurality of center-points along a trajectory of the radiation source, followed by step 615 for identifying, for each of the plurality of center-points, a pair of sections along the trajectory of the scan data, wherein a first section of the pair of sections and a second section of the pair of sections are positioned on opposite sides of the center-point.

A typical center-point may be denoted $s_0$, a first section of a pair may be denoted as $I_-(s_0)$ and a second section of a pair may be denoted as $I_+(s_0)$. The sections should not be too long, so that the amount of object motion during the time the source moves along the section is negligible. For example, the object can be assumed stationary during this time window. At the same time, the length of the section should not be too short and preferably not shorter than a quarter to one-third of one rotation, so that they would allow incomplete reconstruction of a part of the object of interest such that some of its features are clearly recognizable.

In one embodiment, the center-points are equidistant from each other along the trajectory scan and the length of the first and second sections in each pair are equal. In an additional embodiment, the positions of the center-points do not necessarily have to be uniform and the lengths of the sections do not have to be equal. For example, the center-point positions and lengths of pairs of sections along the trajectory of the radiation source could be based upon an external signal that includes motion information of the object of interest. In an exemplary embodiment, an ECG (electrocardiogram) signal could be collected concurrently with the helical scan data and, during times when the cardiac motion of a patient is slow, the center-points could be spaced farther apart, and when the cardiac motion of a patient is fast, the center-points could be spaced closer together. Accordingly, the motion information signal can be used to determine the spacing between each of the plurality of center-points and a location of each of the plurality of center-points. Similarly, when the cardiac motion of a patient is slow, the lengths of the sections in a pair of sections along the trajectory can be increased and when the cardiac motion of a patient is fast, the lengths of the sections in a pair of sections along the trajectory could be decreased. As such, the motion information signal from an external source, such as an ECG, could be used to improve the motion estimation and compensation method.

At a next step 620, the method continues by reconstructing, for each pair of sections, a first partial image from the scan data of the first section and a second partial image from the scan data of the second section. The image reconstructed using scan data corresponding to $I_+(s_0)$ is denoted as $f_{s_0}^+{}_0(\vec{x})$ and the image reconstructed using scan data corresponding to $I_-(s_0)$ is denoted as $f_{s_0}^-(\vec{x})$. The set of points $\vec{x}$, where the images are reconstructed should be the same for both sections. This set of points is denoted as $V(s_0)$. Due to the limited extent of the detector, the set of points is not too large, wherein the set of points is less than approximately a third of the helical pitch along the axis of rotation, and is generally located in a small neighborhood of less than approximately a third of the helical pitch along the axis of rotation of lines (chords) connecting points on $I_+(s_0)$ with points on $I_-(s_0)$. In particular, these reconstructions pertain to a subset of the object of interest. Since the sections of the trajectory $I_+(s_0)$ and $I_-(s_0)$ generally cover a limited angular range, reconstructions of $f_{s_0}^+{}_0(\vec{x})$ and $f_{s_0}^-(\vec{x})$ are referred to as Partial Angle Reconstructions (PARs). The reconstructions of $f_{s_0}^+(\vec{x})$ and $f_{s_0}^-(\vec{x})$ do not have to attempt to recover the attenuation coefficient exactly, they can instead reconstruct a modified image of the object, e.g. with enhanced edges. The main requirement for the reconstruction is that $f_{s_0}^+(\vec{x})$ and $f_{s_0}^-(\vec{x})$ be nearly identical to each other if the object does not have any motion during the scan.

Image registration of the first partial image and the second partial image is then performed at step 625 to estimate a deformation that transforms the first partial image into the second partial image, wherein the deformation is representative of motion of the object of interest during the scan. In performing the image registration, the deformation that transforms one image into another is taken to be an estimate of the deformation that the object is undergoing in a neighborhood of the region $V(s_0)$ at the time close to $s_0$. By interpolating motions estimated in regions $V(s_0)$ for all center-points $s_0$, a global deformation function is obtained for a region of interest in the object of interest. This deformation function has the property that deformation at different points $\vec{x}$ in the object is estimated not for all times, but at fixed times, depending on the time interval when that point was irradiated by the radiation source.

At step 630, the method concludes by generating a motion compensated image by reconstructing the object of interest using the scan data and the estimated deformation.

As such, in various embodiments, the present invention provides an improved system and method for estimating motion and reducing motion artifacts produced during image reconstruction from helical computed tomography scan data The above exemplary embodiment is not meant to be limiting and variations of the exemplary embodiment are within the scope of the present invention.

In general, the method is applicable for more general helical-like trajectories, e.g. variable pitch helices, helices in which the axis of rotation changes somewhat (e.g., as in thermal drift), etc.

Other methods may also be used for computing PARs. Such methods can be based on Local Tomography (LT), or exact or quasi-exact reconstruction.

Instead of estimating the motion (or, equivalently, deformation) of the object, the method can also be used for calibration of the scan (i.e. determination of relevant scan parameters, e.g. position of the central ray, or source-to-center of rotation distance, etc.) In an additional embodiment, the calibration can be performed on the fly during the scan or subsequent to the scan. The calibration can also be performed by finding one set of parameters for the entire scan or by computing these parameters as functions along the scan trajectory.

In various embodiments, the source trajectory may consist of helical-like turns in one direction followed by helical-like turns in the opposite direction.

Conventional method for performing image registration frequency employ an iterative approach, which is time consuming and is difficult to implement. In a specific embodiment, artificial intelligence based methods may be used to perform the image registration of the first partial image and the second partial image to estimate a deformation that transforms the first partial image into the second partial image, wherein the deformation is representative of motion of the object of interest during the scan. In particular, Deep Learning and/or Convolutional Neural Networks (CNN) may be used to perform the image reconstruction of the partial images.

Artificial intelligence based techniques, including Deep Learning and CNN techniques, can be used to perform image registration. In the present invention, a CNN based method is used to perform image registration of partial images acquired from the scans of a subject of interest. Prior to performing the image registration, the CNN is trained using a training dataset comprising a plurality of image pairs. The number of image pairs used for training the CNN may range from a minimum of several hundred to several thousand. In particular, the CNN is trained using successively more difficult training datasets to isolate challenging portions of the PAR registration problem. The training datasets are identified as being more difficult as measured by the complexity of the motion. The easiest case is when all objects are deformed by the same motion. A harder case is when each object is deformed by its own motion. The challenging portions are portions of PARs that are difficult to register accurately. For instance, the most prominent features of PARs could be easy to register accurately, but faint features could be difficult to register In a specific embodiment, a first training dataset may include PAR images deformed by a single motion, to isolate if the PAR image itself poses challenges. A second training dataset may include PAR images deformed by multiple smooth motions with similar dynamic range to the first training dataset, to isolate if smooth motions applied to PAR images are too challenging of a problem. In this context, a problem is challenging if the training process does not converge to a solution that provides the required quality of image registration. A third training dataset may include PAR images deformed by multiple motions, where the data set is created to mimic as closely as possible the real PAR dataset. In this third training dataset identical data augmentation and the same number of images as the original dataset may be used to isolate if the amount of training data is adequate. A fourth training dataset may include PAR images deformed by smooth and local motions, to isolate if localized motion poses special challenges.

Figure 7:
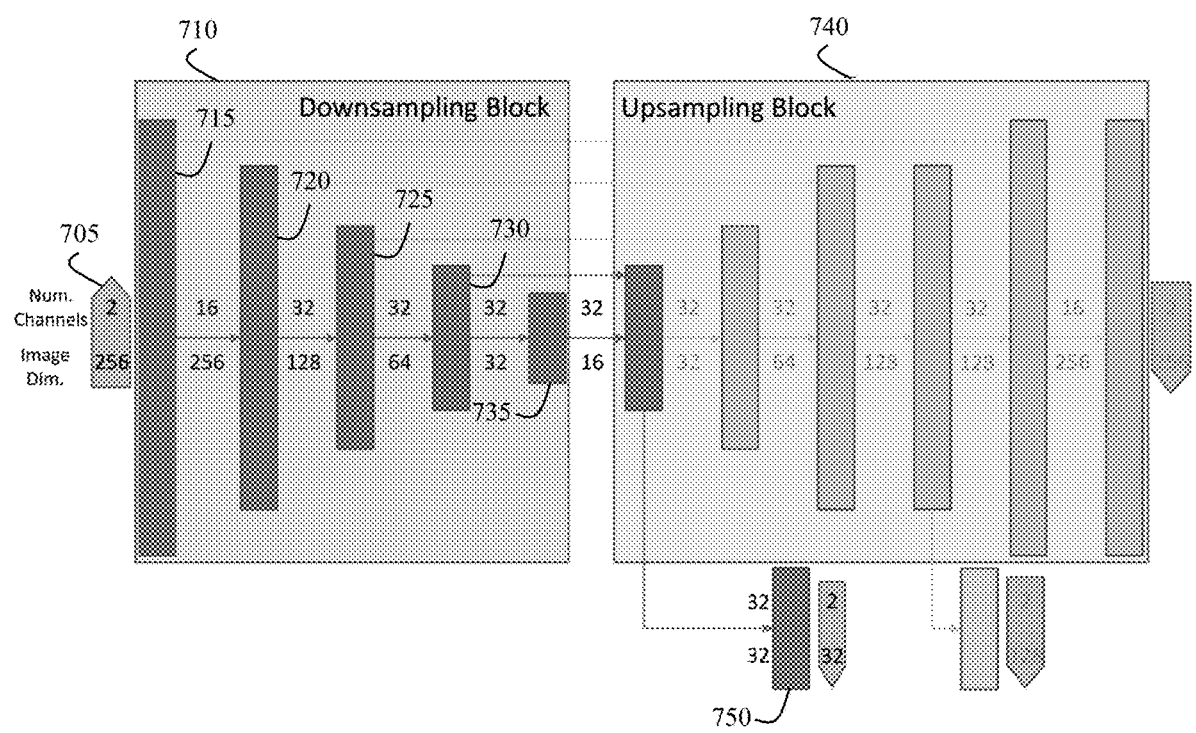
FIG. 7 is an illustration of the method for performing image registration utilizing an artificial intelligence based method, in accordance with an embodiment of the present invention.

As shown in FIG. 7, to perform the image registration of the partial images, a low resolution motion model approach may be utilized to provide a motion model that can be used for motion-compensated reconstruction of final diagnostic images. As illustrated, following the training of the CNN, a pair of PAR images 705 requiring registration are provided to a downsampling block 710 of the CNN. The downsampling block 710 comprises a plurality of successive filters 715, 720, 725, 730, 735 to convolve the images. As such, the pair of PAR images 705 are convolved with the first set of the filters 715 to provide a set of intermediate images. A nonlinear activation function is then applied to the intermediate images, which are then convolved using a second set of filters 720 and the procedure is repeated several times, depending upon the exact architecture of the CNN. While the number of times the procedure is repeated is variable, in various embodiments the number of times may range from as few as single digits to as many as dozens and, more rarely, hundreds of times. After completion of the convolution of the images and application of nonlinear activation functions through the downsampling block 710, the output of the downsampling block 710 may be provided to an upsampling block 740. An output 750 of the upsampling block 725 is the desired deformation map that registers the pair of input images 705. Intermediate images obtained after application of filtration and nonlinear activation functions after steps 715, 720, 725, 730 can also be provided to an upsampling block 740.

Figure 8:
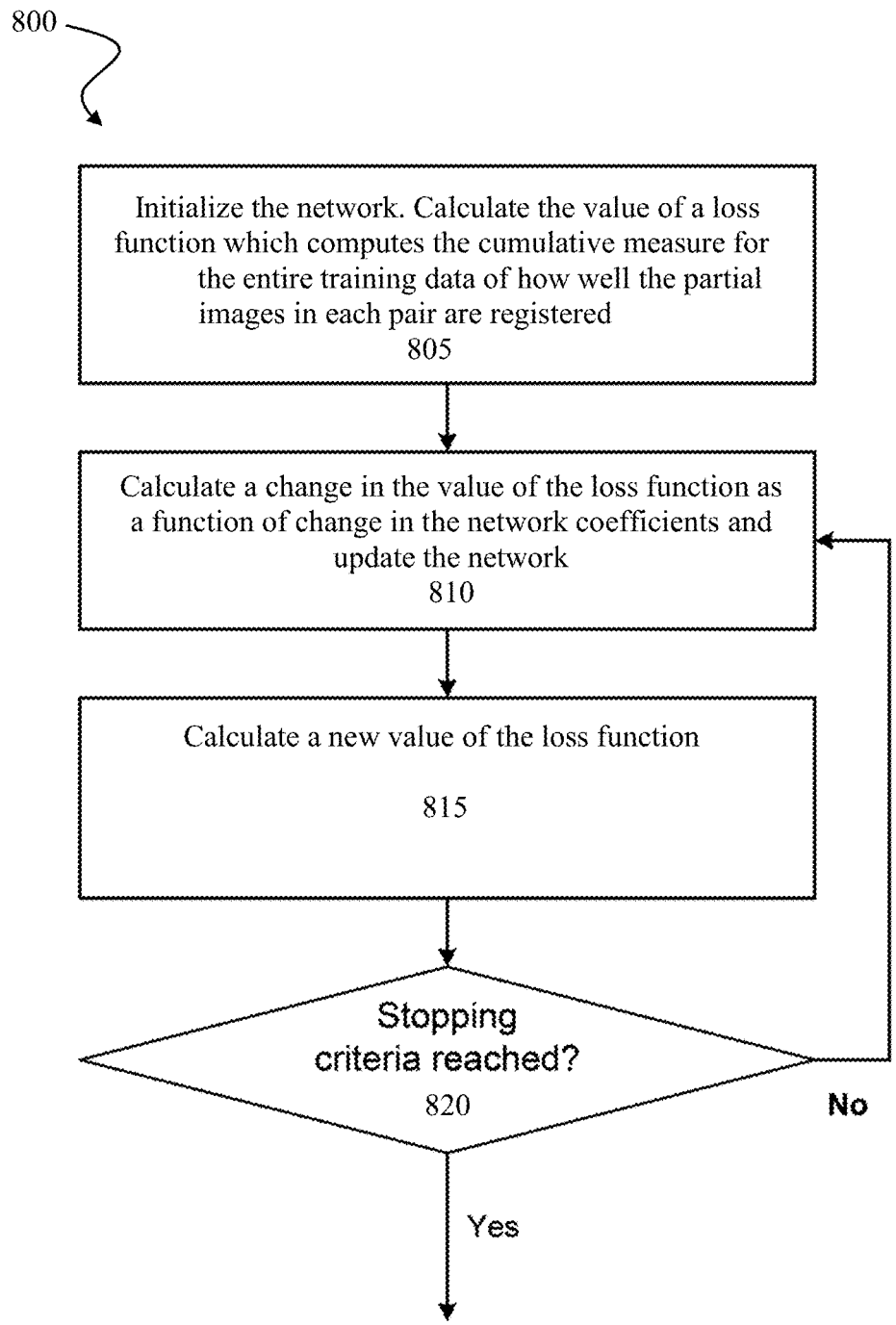
FIG. 8 is a flow diagram illustration a method for training a Deep Leaning network, in accordance with an embodiment of the present invention.

With reference to FIG. 8, a more detailed description of training a Deep Learning (DL) network is provided. Here, the plurality of first partial images and the second partial images are used as input dataset to estimate a deformation that transforms the first partial image into the second partial image in each pair, wherein the output of the DL network is deformation that is representative of motion of the object of interest during the scan, as described above.

FIG. 8 shows a flow diagram of one implementation of the training process 800. In process 800, input data is used as training data to train a DL network, resulting in the DL network being output from step 820 of process 800. The offline DL training process 800 trains the DL network using a large number of the first partial images and the second partial images as input datasets to estimate a deformation that transforms the first partial image into the second partial image.

In step 805 of process 800, the network is initialized and the value of a loss function which computes the cumulative measure for the entire training data of how well the partial images in each pair are registered is calculated. At step 810, a change in the value of the loss function as a function of change in the network coefficients is calculated and the network is updated. At step 815, a new value of the loss function is calculated. At step 820, if a stopping criteria is reached the process terminates and if a stopping criteria is not reached the process returns to step 810 and repeats. For example, the predefined stopping criteria can evaluate whether the new value of the loss function and/or the total number of iterations performed exceed predefined values. In another example, the stopping criteria can be satisfied if either the new value of the loss function falls below a predefined threshold or if a maximum number of iterations is reached.

Steps 805 through 820 of process 800 provide a non-limiting example of an optimization method for training the DL network.

Figure 9:
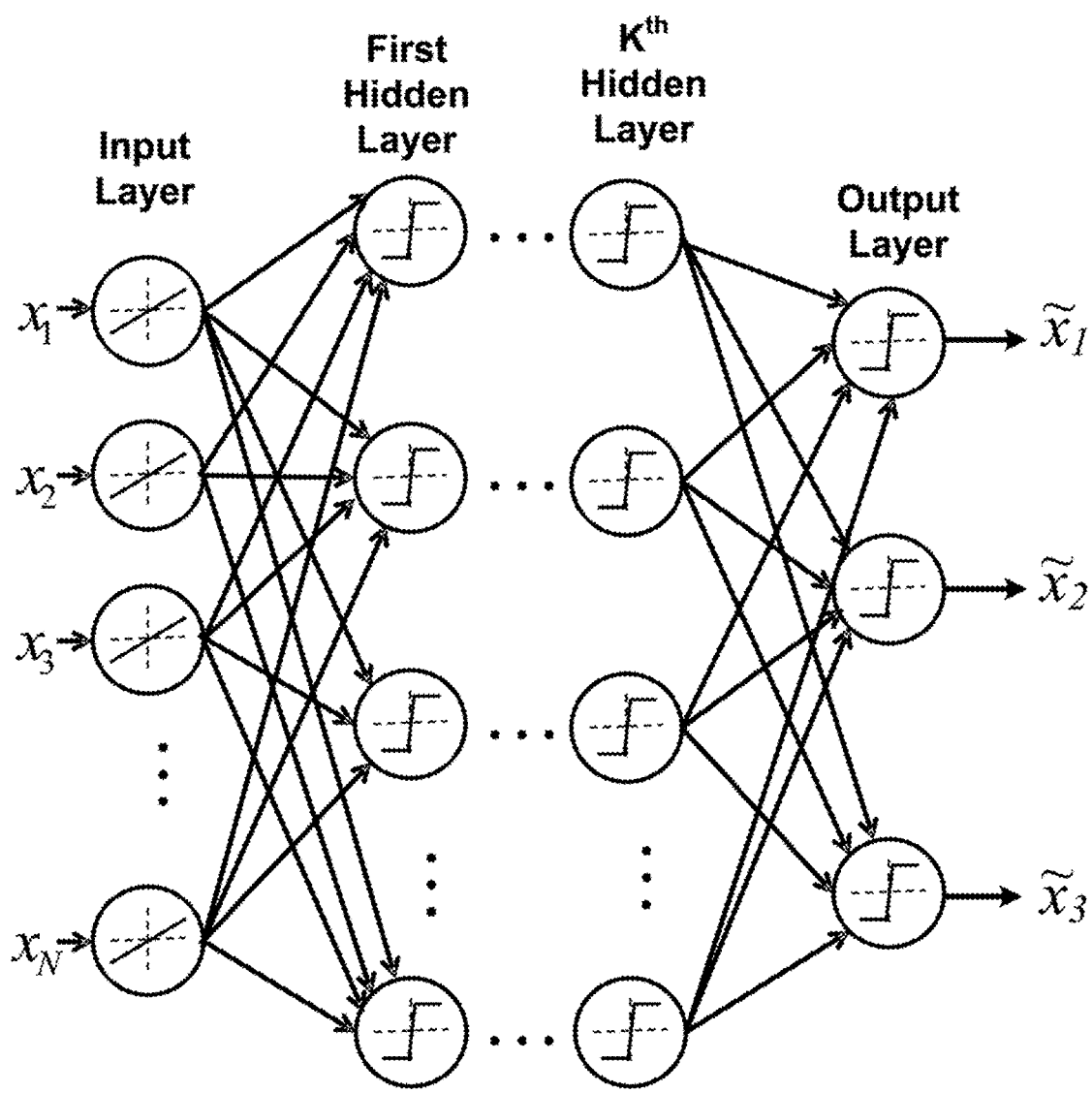
FIG. 9 illustrates an example of a general artificial neural network (ANN) having N inputs, K hidden layers, and three outputs.
Figure 10:
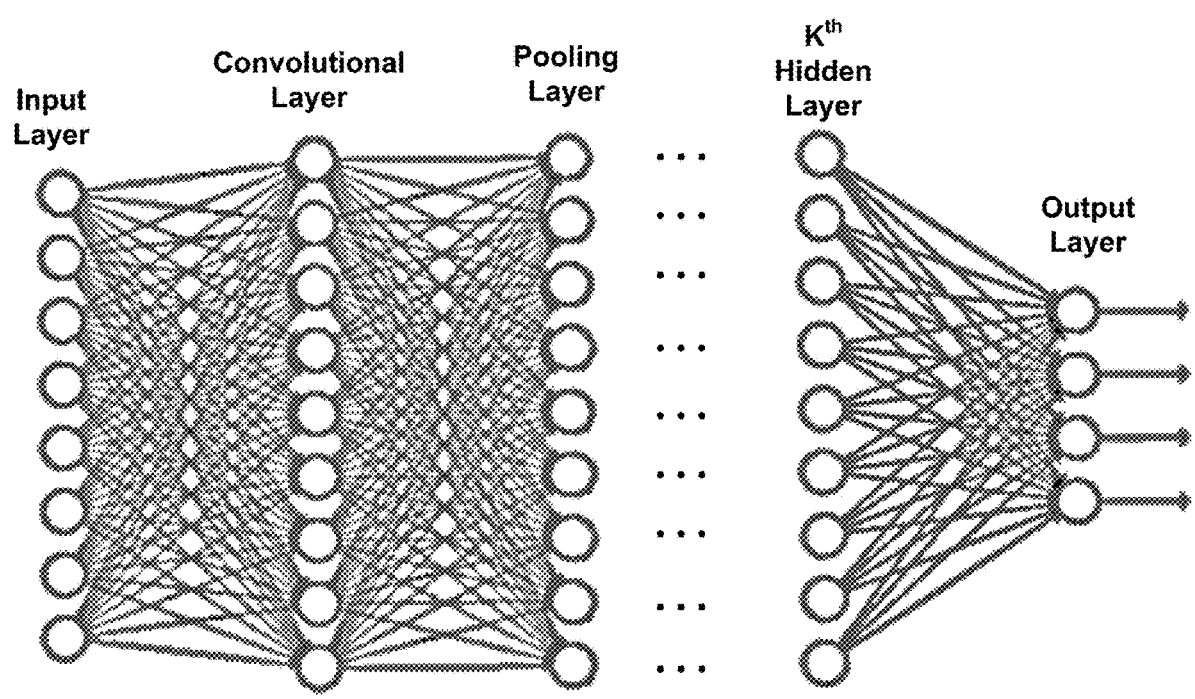
FIG. 10 illustrates a non-limiting example in which the DL network is a convolutional neural network (CNN), in accordance with an embodiment of the present invention.

FIGS. 9 and 10 show two examples of the inter-connections between layers in the DL network. The DL network can include fully connected, convolutional, and the pooling layer, all of which are explained below. In certain preferred implementations of the DL network, convolutional layers are placed close to the input layer, whereas fully connected layers, which perform the high-level reasoning, are place further down the architecture towards the loss function. Pooling layers can be inserted after convolutions and proved a reduction lowering the spatial extent of the filters, and thus the amount of learnable parameters. Activation functions are also incorporated into various layers to introduce nonlinearity and enable the network to learn complex predictive relationships. The activation function can be a saturating activation functions (e.g., a sigmoid or hyperbolic tangent activation function) or rectified activation function (e.g., the Rectified Linear Unit (ReLU) applied in the first and second examples discussed above). The layers of the DL network 170 can also incorporate batch normalization, as also exemplified in the first and second examples discussed above.

FIG. 9 shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m (x) is defined as a composition of other functions $n_i(x)$, which can further be defined as a composition of other functions. This can be conveniently represented as a network structure, with arrows depicting the dependencies between variables, as shown in FIG. 9. For example, the ANN can use a nonlinear weighted sum, wherein $m(x)=K(\Sigma_i w_i n_i(x))$, where K (commonly referred to as the activation function) is some predefined function, such as the hyperbolic tangent.

In FIG. 9 (and similarly in FIG. 10), the neurons (i.e., nodes) are depicted by circles around a threshold function. For the non-limiting example shown in FIG. 9, the inputs are depicted as circles around a linear function, and the arrows indicate directed connections between neurons. In certain implementations, the DL network is a feedforward network.

FIG. 10 shows a non-limiting example in which the DL network is a convolutional neural network (CNN). CNNs are type of ANN that has beneficial properties for image processing, and, therefore, have specially relevancy for the applications of image denoising. CNNs use feed-forward ANNs in which the connectivity pattern between neurons can represent convolutions in image processing. For example, CNNs can be used for image-processing optimization by using multiple layers of small neuron collections which process portions of the input image, called receptive fields. The outputs of these collections can then tiled so that they overlap, to obtain a better representation of the original image. This processing pattern can be repeated over multiple layers having alternating convolution and pooling layers.

Following after a convolutional layer, a CNN can include local and/or global pooling layers, which combine the outputs of neuron clusters in the convolution layers. Additionally, in certain implementations, the CNN can also include various combinations of convolutional and fully connected layers, with pointwise nonlinearity applied at the end of or after each layer.

It has been shown that an AI-based approach to image registration of partial images provides a more efficient method which may prove to be more suitable for motion-compensated reconstruction.

The proposed method of the present invention can be used in conjunction with other motion estimation algorithms. For example, if a preliminary motion model is obtained using fiducial markers, then the proposed algorithm can be used as a second step for finding an improved (i.e. more accurate) motion model.

The present invention may be embodied on various computing platforms that perform actions responsive to software-based methods. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. However, as indicated above, due to circuit statutory subject matter restrictions, claims to this invention as a software product are those embodied in a non-transitory software medium such as a computer hard drive, flash-RAM, optical disk or the like.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like and conventional procedural programming languages, such as the "C" programming language or similar programming languages.

Aspects of the present invention are described with reference to illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method for estimating and compensating for motion by reducing motion artifacts in an image reconstruction from helical computed tomography (CT) scan data of an object of interest, the method comprising:
    collecting helical computer tomography (CT) scan data of an object of interest, wherein the scan data is acquired using a radiation source to generate a cone beam and a radiation detector to detect the cone beam;
    selecting a plurality of center-points along a trajectory of the radiation source;
    identifying a plurality of pairs of sections along the trajectory of the radiation source, wherein each of the plurality of pairs of sections is associated with one of the plurality of center-points and wherein a first section of each of the pairs of sections and a second section of each of the pairs of sections are positioned on opposite sides of the center-point;
    selecting a subset of the plurality of pairs of sections;
    reconstructing, for each pair of the subset, a first partial image from the scan data of the first section and a second partial image from the scan data of the second section;
    performing image registration of the first partial image and the second partial image for each pair of the subset to estimate a deformation that transforms the first partial image into the second partial image, wherein the deformation is representative of motion of the object of interest during the scan and wherein the image registration is performed using an artificial intelligence based method; and
    generating a motion compensated image by reconstructing the object of interest using the scan data and the estimated deformation.

2. The method of claim 1, wherein reconstructing, for each pair of the subset, a first partial image from the scan data of the first section and a second partial image from the scan data of the second section further comprises, reconstructing the first partial image and the second partial image in a region of interest having a substantial overlap.

3. The method of claim 2, further comprising identifying at least one chord between the first section and the second section and wherein reconstructing, for each pair of the subset, a first partial image from the scan data of the first section and a second partial image from the scan data of the second section further comprises, reconstructing the first partial image and the second partial image at a set of points in a neighborhood of at least one chord.

4. The method of claim 1, wherein the first section of each of the plurality of pairs of sections and the second section of each of the plurality of pairs of sections are separated from each other by an angular distance equal to $\pi$.

5. The method of claim 1, wherein the artificial intelligence based method for performing the image registration is selected from a Deep Learning based method and a Convolutional Neural Network (CNN) based method.

6. The method of claim 1, further comprising acquiring a motion information signal and wherein a spacing between each of the plurality of center-points and a location of each of the plurality of center-points is based upon the motion information signal.

7. The method of claim 1, further comprising acquiring a motion information signal and wherein a length of the first section and a length of the second section of the subset is increased or decreased based upon the motion information signal.

8. The method of claim 1, further comprising, prior to performing image registration of the first partial image and the second partial image for each pair of the subset to estimate a deformation that transforms the first partial image into the second partial image further comprises estimating a deformation of a point in the object of interest at a point in time, which is inside an interval of time during which the point was irradiated by the cone beam of the radiation source:
    acquiring a plurality of training images;
    training the artificial intelligence based method by optimizing a performance of the artificial intelligence based method using the plurality of training images to learn one or more parameters for the artificial intelligence based method.

9. The method of claim 1, wherein performing image registration of the first partial image and the second partial image for each pair of the subset to estimate a deformation that transforms the first partial image into the second partial image further comprises:
    convolving the first partial image and the second partial image using a first plurality of filters to generate a first plurality of convolved images;
    performing a nonlinear activation function on the first plurality of convolved images to generate a first plurality of intermediate images;
    convolving the first plurality of intermediate images using a second plurality of filters to generate a second plurality of convolved images;
    performing a nonlinear activation function on the second plurality of convolved images to generate the second plurality of intermediate images; and repeating the steps of convolving the intermediate images using a plurality of filters and performing a nonlinear activation function on the convolved images for a predetermined number of iterations to generate a deformation map that estimates the deformation that transforms the first partial image into the second partial image.

10. The method of claim 1, wherein generating a motion compensated image by reconstructing the object of interest using the scan data and the estimated deformation further comprising, estimating a deformation of the object of interest by interpolating the estimates of deformations for the subset.

11. The method of claim 1, where reconstructing, for each pair of sections of the subset, a first partial image from the scan data of the first section and a second partial image from the scan data of the second section is based upon Local Tomography (LT), exact reconstruction or quasi-exact reconstruction techniques.

12. The method of claim 2, further comprising identifying at least one chord between the first section and the second section for each pair of the subset and reconstructing the first partial image and the second partial image of each pair in a neighborhood of the identified chord to generate a two-dimensional first partial image and a two-dimensional second partial image and performing image registration using the two-dimensional first partial image and the two-dimensional second partial image.

13. The method of claim 2, further comprising identifying a chord surface between the first section and the second section for each pair of the subset and reconstructing the first partial image and the second partial image of each pair in a neighborhood of the identified chord surface to generate a three-dimensional first partial image and a three-dimensional second partial image and performing image registration using the three-dimensional first partial image and the three-dimensional second partial image.

14. A system for estimating and compensating for motion by reducing motion artifacts in an image reconstruction from helical computed tomography (CT) scan data of an object of interest, the method comprising:
a memory for storing a helical computer tomography (CT) scan data of an object of interest;
a data processor for estimating and compensating for motion by reducing motion artifacts in an image reconstruction from the helical computed tomography (CT) scan data of an object of interest, wherein the data processor is adapted for performing the following operations:
loading the helical CT scan data from the memory;
selecting a plurality of center-points along a trajectory of the radiation source;
identifying a plurality of pairs of sections along the trajectory of the radiation source, wherein each of the plurality of pairs of section is associated with one of the plurality of center-points and wherein a first section of each of the pairs of sections and a second section of each of the pairs of sections are positioned on opposite sides of the center-point;
selecting a subset of the plurality of pairs of sections;
reconstructing, for each pair of the subset, a first partial image from the scan data of the first section and a second partial image from the scan data of the second section;
performing image registration of the first partial image and the second partial image for each pair of the subset to estimate a deformation that transforms the first partial image into the second partial image, wherein the deformation is representative of motion of the object during the scan and wherein the image registration is performed using an artificial intelligence based method; and
generating a motion artifact compensated image by reconstructing the object of interest using the scan data and the estimated deformation.

15. The system of claim 14, wherein the artificial intelligence based method is selected from a Deep Learning method and a Convolution Neural Network (CNN) based method.

16. The system of claim 14, wherein the data processor is further adapted for performing the following operations:
convolving the first partial image and the second partial image using a first plurality of filters to generate a first plurality of convolved images;
performing a nonlinear activation function on the first plurality of convolved images to generate a first plurality of intermediate images;
convolving the first plurality of intermediate images using a second plurality of filters to generate a second plurality of convolved images;
performing a nonlinear activation function on the second plurality of convolved images to generate the second plurality of intermediate images; and
repeating the steps of convolving the intermediate images using a plurality of filters and performing a nonlinear activation function on the convolved images for a predetermined number of iterations to generate a deformation map that estimates the deformation that transforms the first partial image into the second partial image.

17. One or more non-transitory computer-readable media having computer-executable instructions for performing a method of estimating and compensating for motion by reducing motion artifacts in an image reconstruction from helical computed tomography (CT) scan data of an object of interest, the method comprising:
collecting helical computer tomography (CT) scan data of an object of interest, wherein the scan data is acquired using a radiation source to generate a cone beam and a radiation detector to detect the cone beam;
selecting a plurality of center-points along a trajectory of the radiation source;
identifying a plurality of pairs of sections along the trajectory of the radiation source, wherein each of the plurality of pairs of sections is associated with one of the plurality of center-points and wherein a first section of each of the pairs of sections and a second section of each of the pairs of sections are positioned on opposite sides of the center-point;
selecting a subset of the plurality of pairs of sections;
reconstructing, for each pair of the subset, a first partial image from the scan data of the first section and a second partial image from the scan data of the second section;
performing image registration for each pair of the first partial image and the second partial image of the subset to estimate a deformation that transforms the first partial image into the second partial image, wherein the deformation is representative of motion of the object of interest during the scan and wherein the image registration is performed using an artificial intelligence based method; and generating a motion artifact compensated image by reconstructing the object of interest using the scan data and the estimated deformation.

18. The media of claim 17, wherein the artificial intelligence based method is selected from a Deep Learning method and a Convolution Neural Network (CNN) based method.

19. The media of claim 17, further comprising instructions for, prior to performing image registration of the first partial image and the second partial image for each pair of the subset to estimate a deformation that transforms the first partial image into the second partial image further comprises estimating a deformation of a point in the object of interest at a point in time, which is inside an interval of time during which the point was irradiated by the cone beam of the radiation source:
  acquiring a plurality of training images;
  training the artificial intelligence based method by optimizing a performance of the artificial intelligence based method using the plurality of training images to learn one or more parameters for the artificial intelligence based method.

20. The media of claim 17, further comprising instructions for:
  convolving the first partial image and the second partial image using a first plurality of filters to generate a first plurality of convolved images;
  performing a nonlinear activation function on the first plurality of convolved images to generate a first plurality of intermediate images;
  convolving the first plurality of intermediate images using a second plurality of filters to generate a second plurality of convolved images;
  performing a nonlinear activation function on the second plurality of convolved images to generate the second plurality of intermediate images; and
  repeating the steps of convolving the intermediate images using a plurality of filters and performing a nonlinear activation function on the convolved images for a predetermined number of iterations to generate a deformation map that estimates the deformation that transforms the first partial image into the second partial image.

* * * * *